United States Patent [19]

Okada

[11] Patent Number: 4,724,836
[45] Date of Patent: Feb. 16, 1988

[54] HIGH-FREQUENCY INCISION TOOL

[75] Inventor: Tsutomu Okada, Tokyo, Japan

[73] Assignee: Olympus Optical Co., Ltd., Tokyo, Japan

[21] Appl. No.: 805,742

[22] Filed: Dec. 6, 1985

[30] Foreign Application Priority Data

Jan. 8, 1985 [JP] Japan ................................. 60-216[U]
May 13, 1985 [JP] Japan ................................. 60-100972

[51] Int. Cl.⁴ ............................................. A61B 17/36
[52] U.S. Cl. ................................. 128/303.15; 128/6
[58] Field of Search .......................................... 128/4–8, 128/303.1, 303.13–303.17

[56] References Cited

U.S. PATENT DOCUMENTS

| | | | |
|---|---|---|---|
| 3,825,004 | 7/1974 | Durden | 128/303.17 |
| 3,910,279 | 10/1975 | Okada et al. | 128/303.15 |
| 4,181,131 | 1/1980 | Ogiu | 128/303.15 |
| 4,325,374 | 4/1982 | Komiya | 128/303.15 |
| 4,485,812 | 12/1984 | Harada et al. | 128/303.15 |
| 4,620,547 | 11/1986 | Boebel | 128/4 |

FOREIGN PATENT DOCUMENTS

| | | |
|---|---|---|
| 2657256 | 6/1978 | Fed. Rep. of Germany ......................... 128/303.15 |
| 2426781 | 12/1981 | Fed. Rep. of Germany ......................... 128/303.15 |

Primary Examiner—Max Hindenburg

[57] ABSTRACT

A high-frequency incision tool has a flexible sheath which is adapted to be inserted into the body cavity along with an endoscope. A suction port is formed at the distal end of the sheath. A wire is inserted into the sheath and a part of the wire is exposed from the sheath to form an incision section. The wire is pushed and pulled by an operating section which is provided at the proximal end of the sheath. A suction mouthpiece is formed at the operating section to communicate with the suction port through the inside passage of the sheath. A reinforcing wire is disposed in the distal end portion of the sheath to reinforce the portion.

10 Claims, 13 Drawing Figures

HIGH-FREQUENCY INCISION TOOL

BACKGROUND OF THE INVENTION

This invention relates to a high-frequency incision tool adapted to be inserted into the body cavity through an endoscope to incise a desired region, e.g., a duodenal papilla.

A so-called papillectomy knife for incising, e.g., an obstructed duodenal papilla, is disclosed in FRG Pat. No. 2,426,781. In general, the papillectomy knife comprises a flexible sheath adapted to be inserted, along with an endoscope, into the body cavity, and a wire extending in the sheath. The wire is exposed to the outside through the middle portion of the sheath, forming an incision section. In incising a duodenal papilla by means of the papillectomy knife, the sheath is located in position as its distal end portion is inserted in a bile duct. To insert the distal end portion of the sheath accurately in the bile duct, bile can be sucked through the distal end portion for examination.

Since the distal end portion of the sheath, which extends from the incision section to the distal end of the sheath, should be inserted in the bile duct, however, it needs to be relatively long. Therefore, the distal end portion will likely bend and prohibit the passage of bile.

SUMMARY OF THE INVENTION

The present invention is contrived in consideration of these circumstances, and is intended to provide a high-frequency incision tool wherein the inside passage of the distal end portion of a sheath is prevented from being closed when it bends.

In order to achieve the above object, a high-frequency incision tool according to the present invention comprises a flexible sheath having an inside passage and electrical insulating capability and adapted to be inserted, along with an endoscope, into the body cavity, the sheath having a suction port at the distal end thereof; a wire inserted into the sheath to conduct a high-frequency current, the wire being exposed from the sheath on the proximal end side thereof with respect to the suction port to form an incision section, and having a distal end portion fixed in the sheath; an operating section provided at the proximal end of the sheath, the operating section including operating means for pushing and pulling the wire and a suction mouthpiece communicating with the suction port through the inside passage of the sheath; and reinforcing means disposed in the sheath, for reinforcing the distal end portion of the sheath extending from the incision section to the suction port.

BRIEF DESCRIPTION OF THE DRAWINGS

FIGS. 1 to 5 show a high-frequency incision tool according to a first embodiment of the present invention, in which

FIGS. 6 and 7 show an incision tool according to a second embodiment of the invention, in which

DETAILED DESCRIPTION OF THE PREFERRED EMBODIMENTS

Several embodiments of the present invention will now be described in detail with reference to the accompanying drawings.

Figure 1:
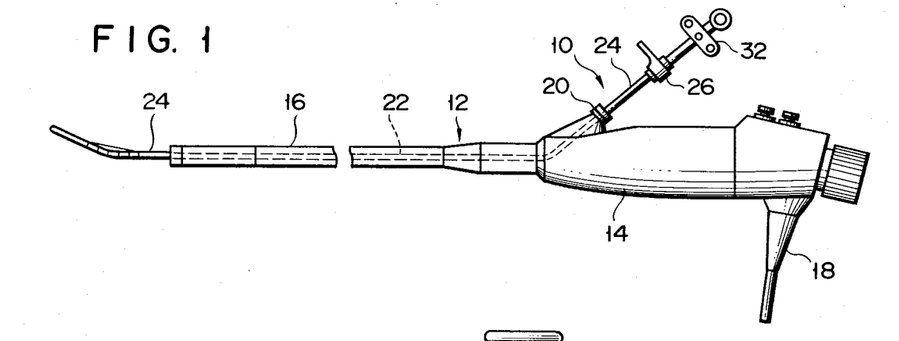
FIG. 1 is a side view showing the incision tool inserted in an endoscope.

FIG. 1 shows high-frequency incision tool 10 according to the invention inserted in endoscope 12. Endoscope 12 comprises operating section 14, insertion section 16 extending from the distal end of operating section 14, and universal cord 18 extending from the proximal end portion of operating section 14. Operating section 14 is provided with insertion mouthpiece 20, from which insertion channel 22 extends through insertion section 16 to the distal end thereof. Sheath 24 of incision tool 10 is inserted in insertion channel 22.

Figure 2:
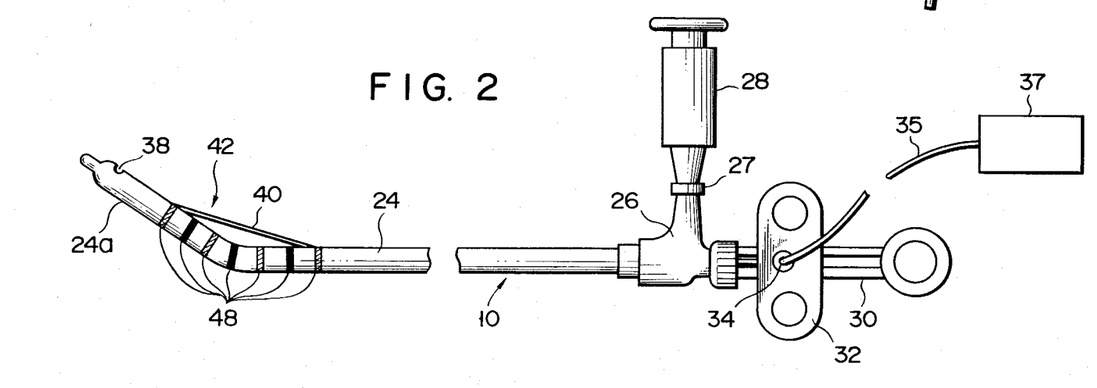
FIG. 2 is a side view of the incision tool.
Figure 3:
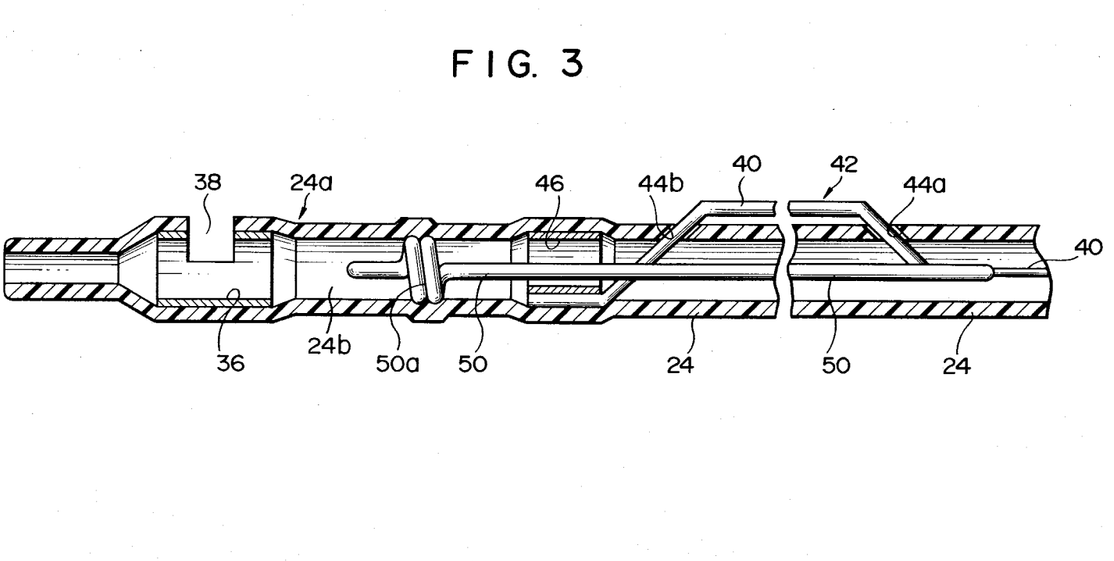
FIG. 3 is a longitudinal sectional view of a sheath.

As shown in FIGS. 2 and 3, incision tool 10 has cylindrical, flexible sheath 24 formed of a transparent insulating material, e.g., synthetic resin. Operating unit body 26 is attached to the proximal end of sheath 24. Body 26 is provided with suction mouthpiece 27 which communicates with inside passage 24b of sheath 24. Suction means, such as syringe 28, is connected to suction mouthpiece 27. A pair of parallel guide rods 30 extend from operating unit body 26, and slider 32 is slidably supported by guide rods 30. Slider 32 has a connecting terminal 34, to which high-frequency current source 37 is connected by means of electric cable 35.

Reinforcing pipe 36 is fitted in the distal end portion of sheath 24. Suction port 38 is bored through the respective peripheral walls of reinforcing pipe 36 and that portion of sheath 24 surrounding pipe 36. Metallic knife wire 40 is inserted in sheath 24. The proximal end of wire 40 is fixed to slider 32. The middle portion of wire 40 is exposed to the outside, constituting incision section 42. A pair of apertures 44a and 44b are bored through those portions of the outer peripheral wall of sheath 24 on the proximal end side thereof with respect to suction port 38, spaced in the axial direction of sheath 24. Wire 40 comes out of sheath 24 through aperture 44a, and then reenters sheath 24 through aperture 44b. The distal end portion of wire 40 is fixed between the inner wall of sheath 24 and the outer wall of fixing pipe 46 which is fitted in sheath 24, located between suction port 38 and incision section 42. Thus, the length of the exposed portion or incision section 42 of knife wire 40 can be changed by pushing or pulling slider 32. Scale 48 is formed on the outer wall of sheath 24, corresponding to incision section 42.

Sheath 24 contains reinforcing wire 50 for reinforcing distal end portion 24a which extends forward from incision section 42. An intermediate portion of reinforcing wire 50 is coiled to form coil portion 50a, which is fixedly fitted in sheath 24, situated between suction port 38 and fixing pipe 46. Reinforcing wire 50 is coated with synthetic resin or another insulating material.

Operation of the high-frequency incision tool with the aforementioned construction will now be described.

Figure 4:
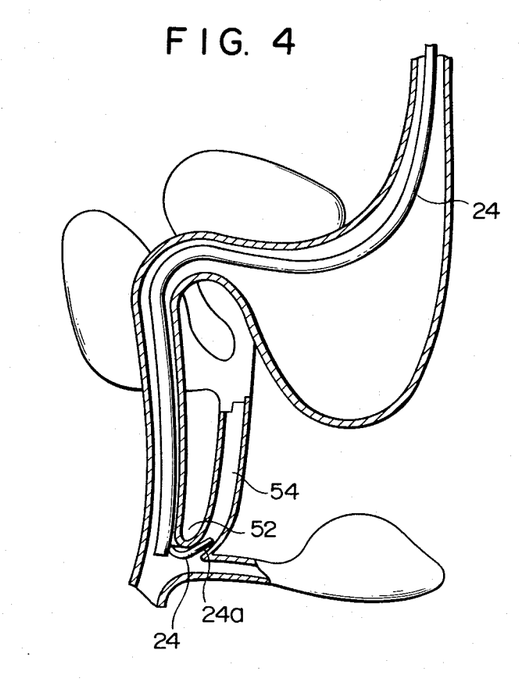
FIG. 4 is a cutaway side view showing the incision tool, along with the endoscope, inserted in a bile duct.
Figure 5:
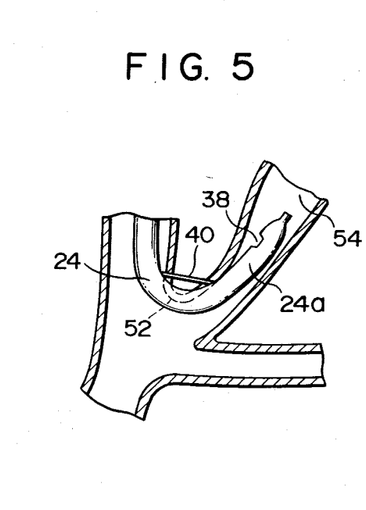
FIG. 5 is an enlarged, cutaway side view showing part of FIG. 4.

In incising a duodenal papilla, for example, insertion section 16 of the endoscope is first inserted into a region near duodenal papilla 52, as shown in FIG. 4. Then, sheath 24 of incision tool 10 is passed through insertion channel 22 of the endoscope, and its distal end portion 24a is projected from the distal end of insertion section 16 into the body cavity. Under endoscopic observation, thereafter, distal end portion 24a of sheath 24 is inserted into bile duct 54 via duodenal papilla 52, as shown in FIGS. 4 and 5. In this state, syringe 28 is connected to suction mouthpiece 27 of operating unit body 26 of incision tool 10, and the body fluid in the body cavity is sucked through suction port 38 and inside passage 24b of sheath 24 by syringe 28. If distal end portion 24a of sheath 24 is in bile duct 54, then bile, the fluid in the bile duct, is sucked into sheath 24. Since bile is yellow, it is possible to check to see if distal end portion 24a is in bile duct 54, by visually examining, through the endoscope, the color of the fluid sucked into sheath 24. If distal end portion 24a is inserted in a wrong region, it can easily be detected from the color of the fluid sucked into sheath 24.

After the position check, distal end portion 24a of sheath 24 is inserted deeper into bile duct 54 so that incision section 42 faces duodenal papilla 52. In this state, slider 32 is manipulated to pull knife wire 40. As a result, knife wire 40 is straightened at incision section 42, and sheath 24 bends. Then, after incision section 42 is brought close to duodenal papilla 52, a high-frequency current is supplied from current source 37 to knife wire 40 through cable 35 and connecting terminal 35. Thus, duodenal papilla 52 is incised by energized wire 40, as shown in FIG. 5.

According to the high-frequency incision tool constructed in this manner, sheath 24 contains therein reinforcing wire 50 for reinforcing distal end portion 24a. In inserting sheath 24 into insertion channel 22 of the endoscope or a desired region in the body cavity, therefore, even when distal end portion 24a of sheath 24 is bent, inside passage 24b is prevented from being closed. Thus, the incision tool can provide secure incision with improved operating efficiency. Also, it is possible to securely suck bile through the inside passage of sheath 24. Since reinforcing wire 50 is coated with an insulating material, moreover, leakage of high-frequency current from wire 50 can be prevented, so that the performance of the incision tool can be maintained.

It is to be understood that the present invention is not limited to the embodiment described above, and that various changes and modifications may be effected therein by one skilled in the art without departing from the scope or spirit of the invention.

Figure 6:
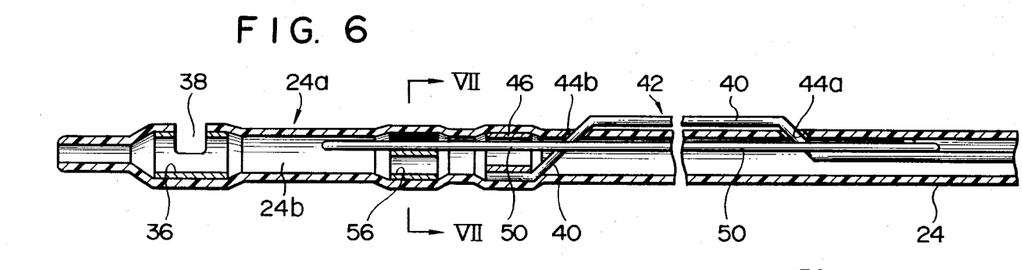
FIG. 6 is a longitudinal sectional view of a sheath.
Figures 7, 8:
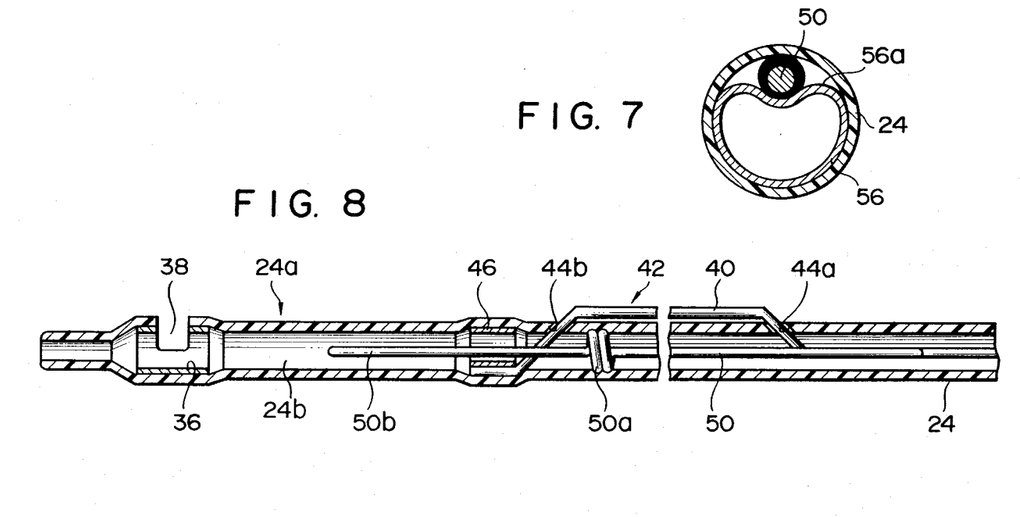
FIG. 7 is a sectional view taken along line VII—VII of FIG. 6.
FIGS. 8 to 13 are longitudinal sectional views of sheaths of incision tools according to third to eighth embodiments of the invention, respectively.

FIGS. 6 and 7 show a second embodiment of the invention. According to this embodiment, reinforcing wire 50 has no coil portion, and is fixed to sheath 24 by means of retaining ring 56. Retaining ring 56 has a depression 56a on its outer wall, and is fitted tight in sheath 24, located between suction port 38 and fixing pipe 46. Reinforcing wire 50 is fixed in depression 56a by soldering.

According to a third embodiment of the invention shown in FIG. 8, reinforcing wire 50 has coil portion 50a in the middle, which is fitted tight in sheath 24 and positioned nearer to the proximal end of sheath 24 than fixing pipe 46. Distal end portion 50b of reinforcing wire 50 projects from coil portion 50a into distal end portion 24a of sheath 24.

Figure 9:
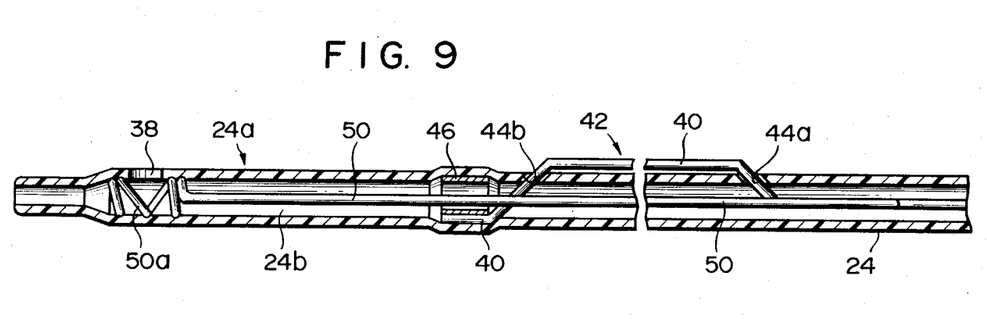

FIG. 9 shows a fourth embodiment of the invention. According to this embodiment, reinforcing wire 50 has coil portion 50a at its distal end. Coil portion 50a is fitted tight in sheath 24, situated corresponding to suction port 38. In this case, reinforcing pipe 36 may be omitted.

Figure 10:
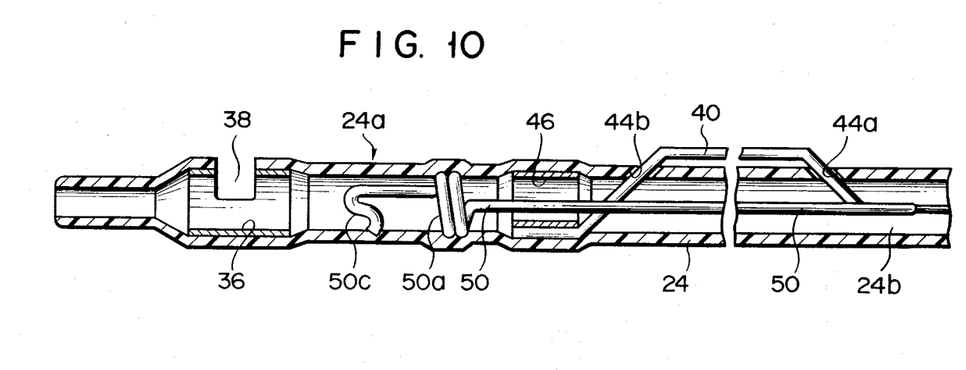

According to a fifth embodiment shown in FIG. 10, reinforcing wire 50 has coil portion 50a in the middle, and its distal end portion is basically S-shaped, forming elastic retaining portion 50c. Coil portion 50a is fitted tight in sheath 24 between suction port 38 and fixing pipe 46, and the extreme end of retaining portion 50c is planted in the inner peripheral surface of sheath 24 by the resiliency of retaining portion 50c.

According to the fifth embodiment, moreover, even if distal end portion 24a bends and reinforcing wire 50 breaks at a point between coil portion 50a and retaining portion 50c, the broken piece of wire 50 can be prevented from falling off sheath 24 by retaining portion 50c.

Figure 11:
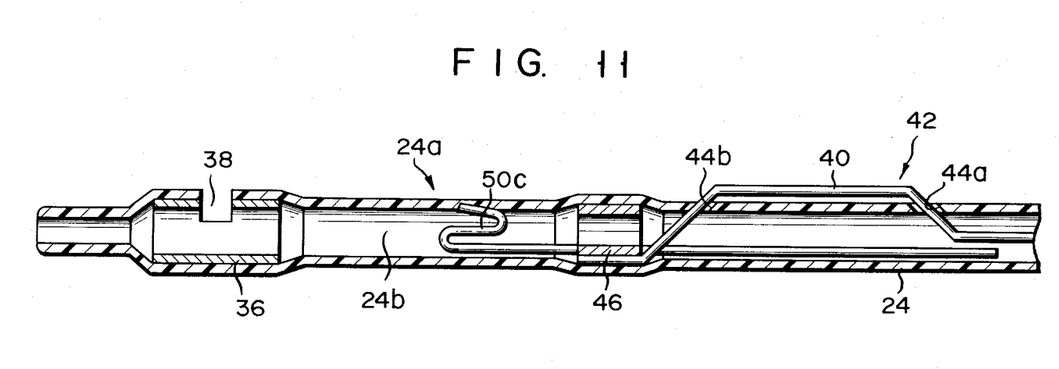

According to a sixth embodiment shown in FIG. 11, reinforcing wire 50 has no coil portion. The middle portion of wire 50 is fixed to fixing pipe 46, and the distal end portion is basically S-shaped, forming elastic retaining portion 50c. The extreme end of retaining portion 50c is planted in the inner wall of sheath 24.

Figure 12:
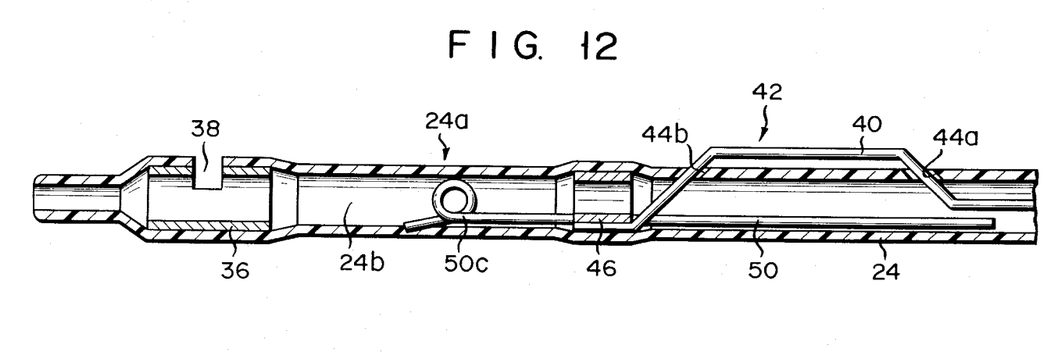

According to a seventh embodiment shown in FIG. 12, retaining portion 50c of reinforcing wire 50 is formed in a loop and the extreme end of retaining portion 50c is planted in the inner wall of sheath 24.

Figure 13:
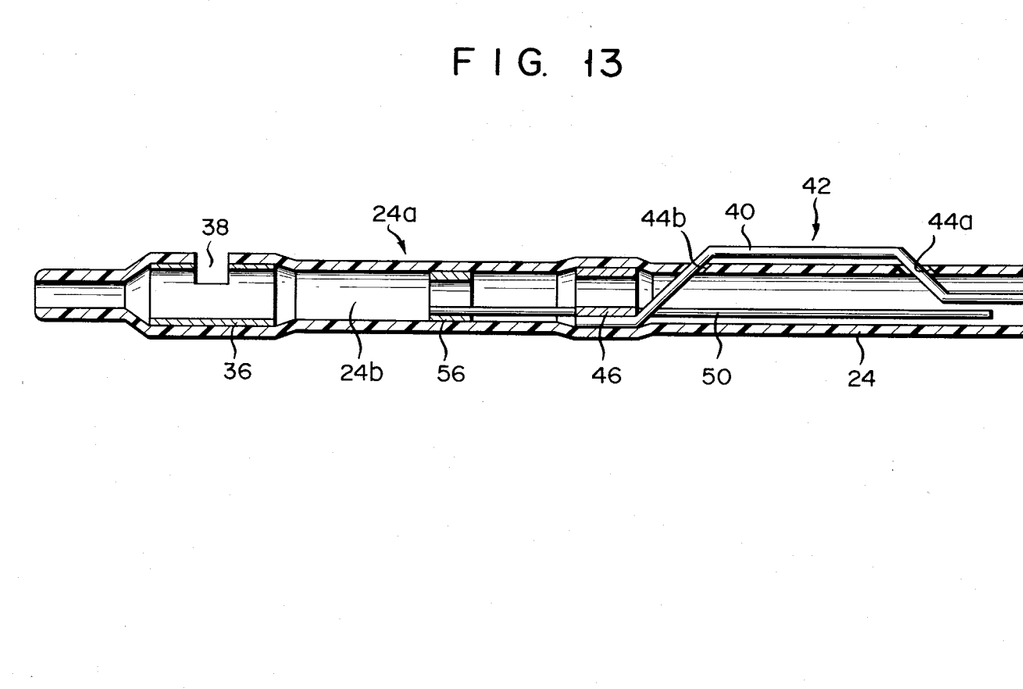

According to a eighth embodiment shown in FIG. 13, retaining portion 50c of reinforcing wire 50 is formed in a straight shape, and is fixed to sheath 24 by means of retaining ring 56.

The sixth to eighth embodiments are provided with the same effects as that of the fifth embodiment.

In the second to eighth embodiments described above, like reference numerals are used to designate like members as included in the first embodiment.

What is claimed is:

1. A high-frequency incision tool for insertion into a body cavity through an endoscope to incise a desired region in the body cavity by means of a high-frequency current supplied from a high-frequency current source, comprising:

a flexible sheath having an inside passage, and a suction port at a distal end thereof, said sheath being insulated electrically and insertable, along with the endoscope, into the body cavity;

a wire inserted into the sheath of conduct the high-frequency current, said wire being exposed from a portion of the sheath which is closer to a proximal end thereof than the suction port, to form an incision section, and having a distal end portion fixed in the sheath;

an operating section provided at the proximal end of the sheath, said operating section including operating means connected to the wire, for pushing and pulling the wire, and a suction mouthpiece communicating with the suction port through the inside passage of the sheath; and a reinforcing wire disposed in the sheath, for reinforcing the distal end portion of the sheath, said reinforcing wire having a straight portion extending axially within the distal end portion of the sheath over the entire length of the incision section, and a non-linear portion connected to the straight portion, fixed to the inside passage, and of a length considerably shorter that said straight portion so as to insure smooth flow of body fluids from said suction port through said incision section.

2. The incision tool according to claim 1, wherein the middle portion of said reinforcing wire is coiled to form a coil portion fitted in the sheath to be in close contact with the inner surface of the sheath.

3. The incision tool according to claim 2, wherein said coil portion is located between the suction port and the incision section.

4. The incision tool according to claim 2, wherein said coil portion is fitted in the sheath to be located corresponding to the incision section.

5. The incision tool according to claim 1, wherein the distal end portion of said reinforcing wire is coiled to form a coil portion fitted in the sheath to be in close contact with the inner surface of the sheath.

6. The incision tool according to claim 1, wherein the middle portion of the reinforcing wire is fixed to the sheath, and the distal end portion of the reinforcing wire is bent to form an elastic retaining portion engaging the inner surface of the sheath.

7. The incision tool according to claim 6, wherein the middle portion of said reinforcing wire is coiled to form a coil portion fitted in the sheath to be in close contact with the inner wall of the sheath.

8. The incision tool according to claim 1, wherein said reinforcing wire is covered with an electric insulating material.

9. The incision tool according to claim 1, wherein said suction port is formed in the peripheral wall of the sheath.

10. The incision tool according to claim 1, comprising a retaining pipe fitted in the sheath and located between the suction port and the incision section, said reinforcing wire being fixed to the retaining pipe.

* * * * *